United States Patent
Ketonis et al.

(10) Patent No.: US 11,957,517 B2
(45) Date of Patent: Apr. 16, 2024

(54) AUTOMATED ULTRASOUND ASSESSMENT OF TENDON HEALING AND ANALYSIS/UTILIZATION OF RESULTS USING ARTIFICIAL INTELLIGENCE

(71) Applicant: University of Rochester, Rochester, NY (US)

(72) Inventors: Constantinos Ketonis, Rochester, NY (US); Alayna E. Loiselle, Rochester, NY (US)

(73) Assignee: University of Rochester, Rochester, NY (US)

( * ) Notice: Subject to any disclaimer, the term of this patent is extended or adjusted under 35 U.S.C. 154(b) by 343 days.

(21) Appl. No.: 17/436,729

(22) PCT Filed: Mar. 4, 2020

(86) PCT No.: PCT/US2020/020881
§ 371 (c)(1),
(2) Date: Sep. 7, 2021

(87) PCT Pub. No.: WO2020/185455
PCT Pub. Date: Sep. 17, 2020

(65) Prior Publication Data
US 2022/0183662 A1  Jun. 16, 2022

Related U.S. Application Data

(60) Provisional application No. 62/817,760, filed on Mar. 13, 2019.

(51) Int. Cl.
*A61B 8/08* (2006.01)
*A61B 5/00* (2006.01)
(Continued)

(52) U.S. Cl.
CPC .......... *A61B 8/5223* (2013.01); *A61B 5/4523* (2013.01); *A61B 8/08* (2013.01);
(Continued)

(58) Field of Classification Search
None
See application file for complete search history.

(56) References Cited

U.S. PATENT DOCUMENTS

2018/0055479 A1* 3/2018 Lalena ................ A61B 8/4461

OTHER PUBLICATIONS

Ackerman et al., "Non-invasive ultrasound quantification of scar tissue volume predicts functional changes during tendon healing". University of Rochester Medical Center, Nov. 4, 2018 (https://www.biorxiv.org/content/10.1101/460790v1). (Year: 2018).*

(Continued)

*Primary Examiner* — Yi-Shan Yang
(74) *Attorney, Agent, or Firm* — Wissing Miller LLP

(57) ABSTRACT

Specialized ultrasound imaging systems and methods provide metrics related to objective and consistent quantification of scar tissue volume that strongly correlate with tendon healing and range of motion. Automated acquisition of ultrasound images of fingers helps assess tendon healing in a non-invasive, quantitative fashion and can be used to guide clinical decision-making, management of post-operative tendon repair patients, and employment and insurance considerations.

20 Claims, 8 Drawing Sheets

(51) Int. Cl.
  *A61B 8/00* (2006.01)
  *A61B 8/14* (2006.01)
  *G06T 7/00* (2017.01)

(52) U.S. Cl.
  CPC .............. *A61B 8/14* (2013.01); *A61B 8/4209* (2013.01); *A61B 8/4281* (2013.01); *A61B 8/4461* (2013.01); *A61B 8/4483* (2013.01); *A61B 8/467* (2013.01); *A61B 8/483* (2013.01); *A61B 8/565* (2013.01); *G06T 7/0012* (2013.01); *G06T 2207/10136* (2013.01); *G06T 2207/20081* (2013.01); *G06T 2207/20084* (2013.01); *G06T 2207/30088* (2013.01)

(56) References Cited

OTHER PUBLICATIONS

Rubery et al., "URMC researchers collaborate to automate ultrasound interpretation"., In Motion, UR Medicine Orthopaedics and Rehabilitation News, vol. 16, Fall 2018, p. 7. (Year: 2018).*
International Search Report in PCT/US2020/020881, dated Sep. 10, 2020.
De Putter CE, Selles RW, Polinder S, Panneman MJ, Hovius SE, and van Beeck EF. Economic impact of hand and wrist injuries: health-care costs and productivity costs in a population-based study. J Bone Joint Surg Am. 2012;94(9):e56.
Galatz LM, Gerstenfeld L, Heber-Katz E, and Rodeo SA Tendon regeneration and scar formation: The concept of scarless healing. J Orthop Res. 2015;33(6):823-31.
Beredjiklian PK. Biologic aspects of flexor tendon laceration and repair. J Bone Joint Surg Am. 2003;85-A(3):539-50.
Lin T. Biomechanics of tendon inury and repair. Journal of biomechanics. 2004;37:865-77.
Aydin A, Topalan M, Mezdegi A, Sezer I, Ozkan T, Erer M, et al. [Single-stage flexor tendoplasty in the treatment of flexor tendon injuries]. Acta Orthop Traumatol Turc. 2004;38(1):54-9.
Shelhamer E, Long J, Darrell T. Fully Convolutional Networks for Semantic Segmentation. IEEE Trans Pattern Anal Mach Intell. 2017;39(4):640-51.
De Jong JP, Nguyen JT, Sonnema AJ, Nguyen EC, Amadio PC, and Moran SL. The incidence of acute traumatic tendon injuries in the hand and wrist: a 10-year population-based study. Clinics in orthopedic surgery. 2014;6(2):196-202.
Everingham M, Eslami SMA, Van Goal L, Williams CKI, Winn J, Zisserman A. The PASCAL Visual Object Classes Challenge: A Retrospective. Int J Comput Vision. 2015;111(1):98-136.
Milletari F. V-Net: Fully Convolutional Neural Networks for Volumetric Medical Image Segmentation. arXiv.2016;1606.04797.
Betrouni N, Puech P, Dewalle AS, Lopes R, Dubois P, Vermandel M. 3D automatic segmentation and reconstruction of prostate on MR images. Conf Proc IEEE Eng Med Biol Soc. 2007;2007:5259-62.
Wong J, Bennett W, Ferguson MW, McGrouther DA. Microscopic and histological examination of the mouse hindpaw digit and flexor tendon arrangement with 3D reconstruction. J Anat. 2006;209(4):533-45.

* cited by examiner

UN-INJURED TENDON

DAY 14 POST-SURGERY

AUTOMATED ULTRASOUND ASSESSMENT OF TENDON HEALING AND ANALYSIS/UTILIZATION OF RESULTS USING ARTIFICIAL INTELLIGENCE

PRIORITY CLAIM

This application is a continuation-in-part and a National Stage of International Patent Application PCT/US2020/020881 filed Mar. 4, 2020, which claims the benefit of U.S. Provisional Application No. 62/817,760, filed Mar. 13, 2019. The contents of said two applications are hereby incorporated by reference.

FIELD

This patent specification pertains to devices and methods for ultrasound imaging of tissue, improving imaging, and deriving and using imaging results. Some aspects pertain to imaging tendons and scar tissue formed after injury of tendons, including flexor tendons in the hand and scar tissue formed after traumatic injury of such tendons. Still other aspects pertain to improving and utilizing the images and deriving objective results. Yet other aspects pertain to assessing prognosis and guiding treatment.

BACKGROUND

The numbers in parenthesis below identify references that are listed at the end of this specification and are incorporated herein by reference.

Flexors tendons (FTs) in the hand are located on the palmar surface and are responsible for both gross and fine movement of the fingers. The relatively superficial anatomic location of the FTs makes them susceptible to traumatic injury. FT injuries are common, with hand injuries accounting for 10% of emergency room visits, and up to 20% of all injuries treated (1). Hand injuries are among the most expensive based on both direct costs and lost productivity, as over 87% of occupational hand injuries occur in the active workforce (16-54 years old), resulting in a loss of over 700,000 workdays per year (Dept. of Labor, 2016). Moreover, hand injury costs exceed those of lower limb and hip fractures, and skull-brain injuries (2).

FT injuries heal with a scar tissue response, a process that is conserved among all tendons (3). However, the anatomic constraints of the FT-synovial sheath compartment make this pathological healing process particularly problematic. Uninjured FTs glide through the synovial sheath in a near frictionless-manner. However, after injury, adhesions form between the FT and synovial sheath, impairing FT gliding function and restricting digit range of motion (ROM) and hand function (4, 5). Up to 40% of primary FT injuries will result in significant adhesion formation (6) and impairments in finger function. It is often difficult for surgeons to determine whether impaired hand/finger function after flexor tendon repair is due to adhesion formation, or if the repair has been plagued by common complications including re-rupture or gapping at the repair site. Making the distinction between adhesion formation, which may be managed more conservatively at first, and re-rupture or gapping that will necessitate more expedient surgical management, is an important clinical determinant for which there is no known objective diagnostic tool.

SUMMARY OF THE DISCLOSURE

Figure 1:
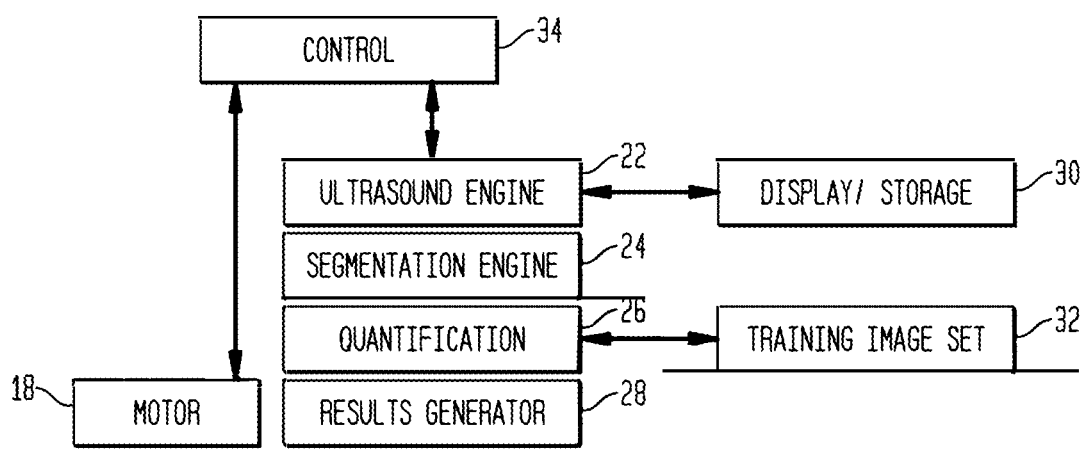
FIG. 1 illustrates automated acquisition of ultrasound images and equipment to process the images and generate useful results, according to some embodiments.
Figure 1:
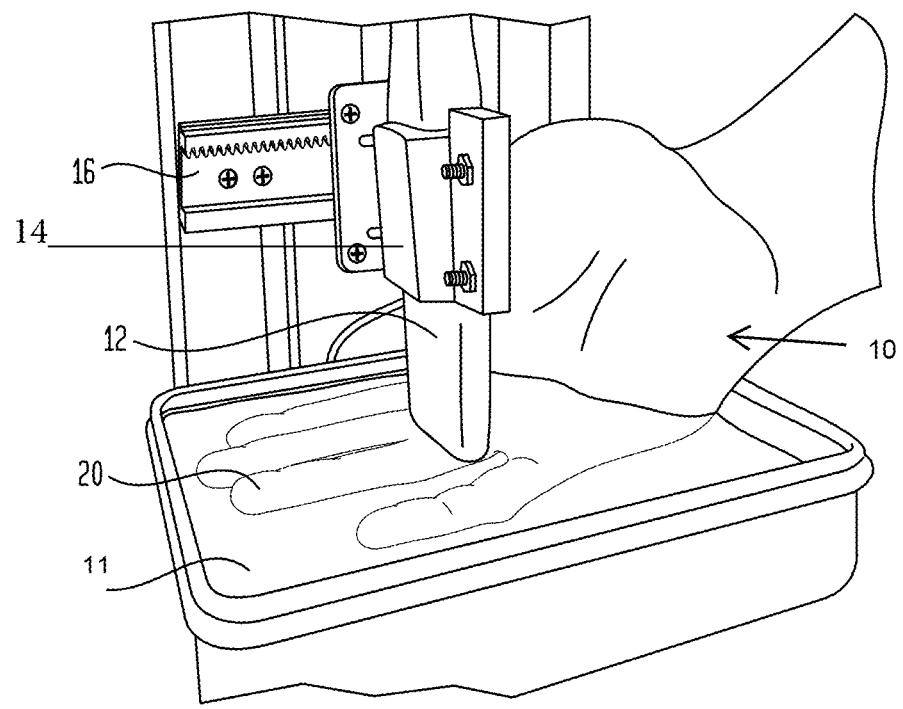

This patent application describes a novel ultrasound-based imaging approach that facilitates visualizing and assessing adhesion formation and flexor tendon healing and utilizing results. Unique ultrasound hardware takes a series of two-dimensional (2D) images of the hand or finger with injured tendon, which can be axial (conforming to planes transverse to the length of a finger) and/or longitudinal (conforming to planes along the length of a finger, e.g., sagittal) and processes them into three-dimensional (3D) images and/or improved 2D images that differ in orientation or other characteristics such as spatial or contrast resolution. Automated, computer-implemented segmentation algorithms act on these images to differentiate between scar tissue, tendons, and/or other tissue and to estimate scar tissue volume and possibly other tissue characteristics. Further computer-implemented processing determines the degree of direct and/or inverse correlation between direct or processed results of the segmentation and metrics of healing such as metatarsophalangeal (MTP) range of motion (ROM). The images and correlation and other results can be utilized in further automated, computer-implemented or computer-assisted processes to assess the healing process and prognosis, to guide treatment, to classify the degree of disability of a subject, to plan and assess different treatments, etc.

According to some embodiments, a system for ultrasound imaging of tendon regions comprises: an ultrasound image acquisition unit including an ultrasound transducer, a support for a patient's body part containing a tendon, a coupling agent for acoustic coupling of the transducer to the body part on the support, and an automated drive moving the transducer in a selected trajectory relative to the body part on the support to take ultrasound images thereof; an automated, computer-implemented segmentation facility configured to segment scar tissue from said images and/or a three-dimensional representation of the imaged body part and derive a quantified scar tissue estimate of scar tissue in a selected volume of the body part; an automated, computer-implemented facility configured to test the quantified scar tissue estimate against parameters derived from a multiplicity of teaching ultrasound images of scar tissue associated with respective known tendon healing parameters and derive a quantified estimate of expected healing parameters for the finger; and an automated, computer-implementing facility using the estimate of expected healing parameter of the finger to provide one or more parameters pertaining to a treatment guide, medication dosing, and disability classification. According to some embodiment the ultrasound system further includes one or more of the following features: (a) the body part is elongated and the acquisition unit is configured to scan the body part and provide a series of sagittal views spaced from each other along a width of the elongated body part by selected consistent intervals; (b) the body part is elongated and the acquisition unit is configured to scan the body part and provide a series of axial views spaced from each other along a length of the body part by selected consistent intervals; (c) the coupling agent comprises a liquid in which the body part being imaged is inserted; (d) the body part is a patient's finger; and (e) the automated, computer-implementing facility is configured to apply artificial intelligence algorithms to said estimates.

According to some embodiments a method of ultrasound imaging of tendon regions comprises: acquiring ultrasound images of a body part that contains a tendon while supporting the body part and scanning the body part with an ultrasound transducer driven by a motor in a selected trajectory relative to the body part; segmenting scar tissue from said images and/or a three-dimensional representation of the imaged body part of tendon using an automated, computer-implemented image processing to derive a scar tissue estimate of scar tissue in a selected volume of the body part; testing the scar tissue estimate against parameters derived from a multiplicity of teaching ultrasound images of scar tissue associated with respective known tendon healing parameters and deriving an estimate of expected healing parameters for the tendon using an automated, computer-implemented facility; and using the estimate of expected healing parameter of the tendon to provide one or more of a treatment guide, medication dosing, and disability classification with an automated, computer-implementing facility. According to some embodiments, the method further includes one or more of the following features: (a) the body part is elongated and the acquisition comprises providing a series of sagittal views spaced from each other along a width of the body part by selected consistent intervals; (b) the body part is elongated and the acquisition unit is configured to provide a series of axial views spaced from each other along a length of the body part by selected consistent intervals; and (c) the body part is a patient's finger.

DETAILED DESCRIPTION OF PREFERRED EMBODIMENTS

A detailed description of examples of preferred embodiments is provided below. While several embodiments are described, the new subject matter described in this patent specification is not limited to any one embodiment or combination of embodiments described herein and encompasses numerous alternatives, modifications, and equivalents. In addition, while numerous specific details are set forth in the following description to provide a thorough understanding, some embodiments can be practiced without some or all these details. Moreover, for the purpose of clarity, certain technical material that is known in the related art has not been described in detail, to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

FIG. 1 illustrates an example of equipment to acquire ultrasound images of hand tendon injuries and healing and to use the resulting images to generate results facilitating treatment and providing other benefits. A patient's hand 10 is immersed in liquid such as a water bath 11 ensuring good acoustic coupling with an ultrasound transducer 12 held in a support 14 that is driven linearly along a track 16 by a motor 18 to scan a finger 20 along the fingers length. In this scanning motion, transducer 12 generates a series of ultrasound images under control of an ultrasound engine 22 and supplies them to engine 22 for further processing. Alternatively, good acoustic coupling can be achieved using gel. The images can be cross-sections (axial views) of the hand or finger or at least a portion with tendon damage, as illustrated in FIG. 1, or longitudinal (e.g. sagittal) views of the hand or a finger and transducer are oriented differently. Transducer 12 can use a single row of transducer elements or multiple rows. One example of a suitable transducer is a 15 MHz transducer model no. HFL50X available from SonoSite (FujiFilm). Other transducers, with different characteristics, can be used instead to acquire the desired images. One example of ultrasound engine 22 is an ultrasound machine model SonoSite Sli (FujiFilm). Other commercially available ultrasound machines can be used, such as Butterfly iQ or larger machines from companies such as GEHealthcare and Siemens.

FIG. 1 additionally illustrates equipment for making use of ultrasound images that units 12 and 22 generate. This additional equipment, the function and operation of which are described in more detail further below, includes: a segmentation engine 24 that automatically segments scar tissue from two-dimensional (2D) ultrasound images and/or from three-dimensional (3D) images generated from the 2D images; a quantification engine 26 that quantifies the segmented scar tissue, for example by volume and/or in relation to parameters such as the size of the finger; and a results generator 28 that uses the quantifications from engine 26 to produce results such as metrics or indicators that can guide personalized treatment options for the patient, help determine treatment outcomes, classify the degree of disability, etc. FIG. 1 still further illustrates a display and storage unit 30 that displays images and results from units 22-28 and stores them or transmits them to other locations such as workstations or PACS storage or cloud storage. A storage unit 32 can be used to store and provide training ultrasound images for use by units 24-28. A control unit 34 controls the operation of the equipment and interacts with commands by a user, for example through a keyboard, a mouse, or a touch-sensitive screen. Units 22-34 can be integrated into a single enclosure or two or more enclosures and can be implemented in a suitable combination of hardware, firmware, and computer-implemented controlling algorithms.

Figure 2:
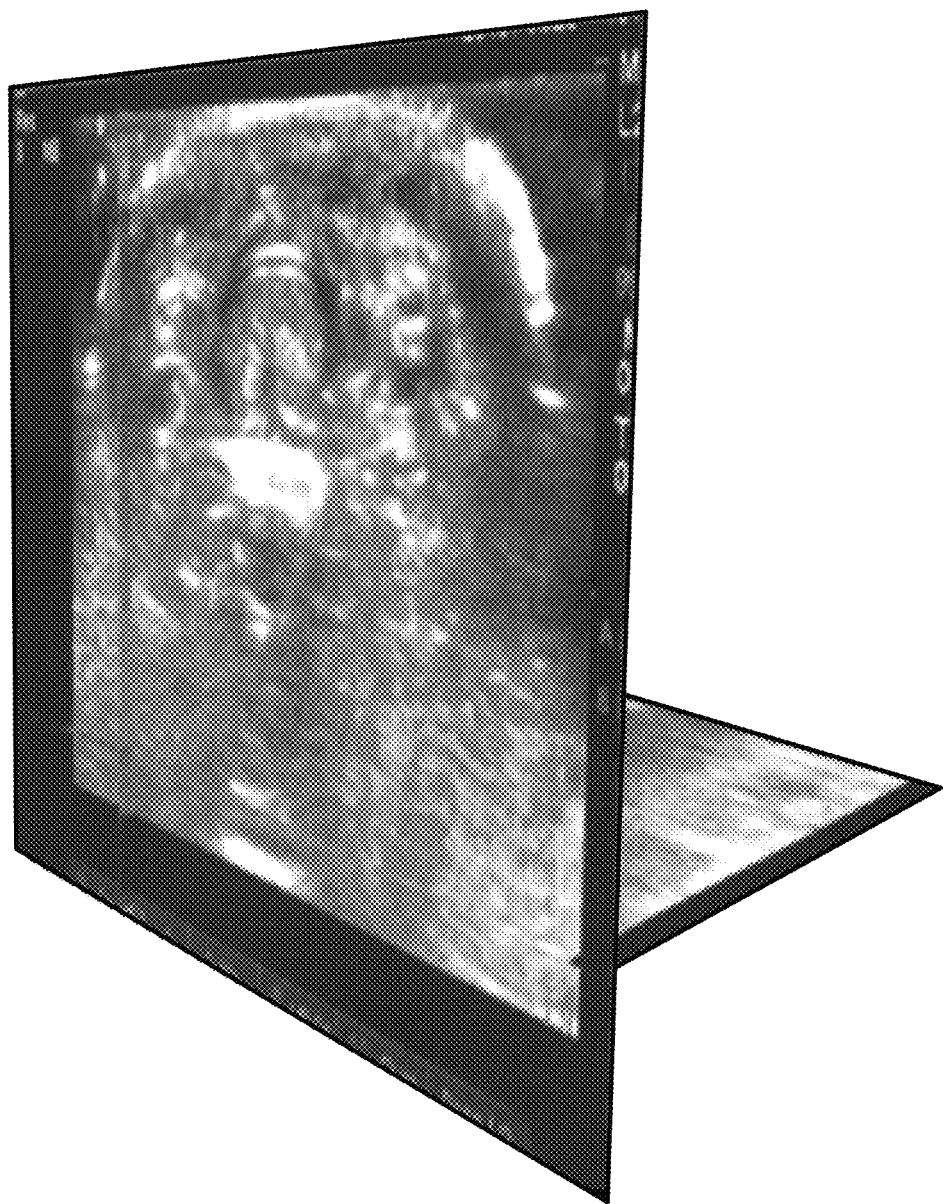
FIG. 2 illustrates and example of a cross-sectional (axial) ultrasound image of a tendon and surrounding tissue, according to some embodiments.

FIG. 2 illustrates an axial (cross-sectional) ultrasound image of a finger. Transducer 12 can take such images at selected distance intervals as it scans along the length of the finger, for example every 0.2 mm or every 1 mm or some other interval in distance to generate axial section views. Alternatively, transducer 12 can operate essentially continuously and generate a video clip of such images. An important benefit of the arrangement illustrated in FIG. 1 is that such images are consistent with each other within the same finger and among different fingers in terms of parameters such as spacing, orientation, and other characteristics, in contrast with images taken in manual scanning with an ultrasound transducer. Alternatively, or in addition, transducer 12 can scan in a direction transverse to the length of a finger, to generate a series or a video of longitudinal, e.g., sagittal, views or a video clip that show longitudinal portions of a tendon. For such longitudinal images, the hand is rotated a quarter turn relative to the orientation illustrated in FIG. 1.

Figure 3:
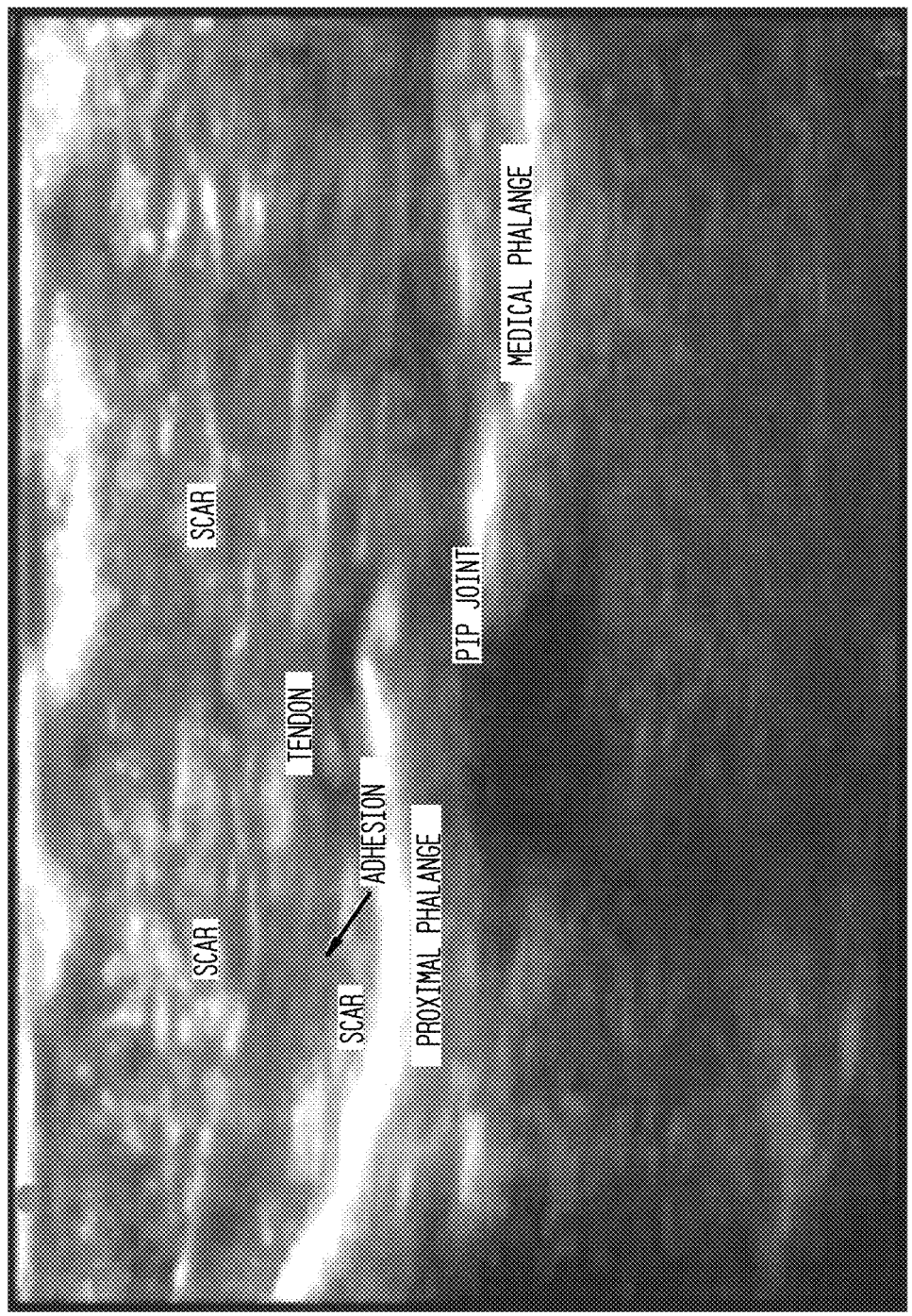
FIG. 3 illustrates an example of a longitudinal (sagittal in this case) ultrasound image of a tendon and surrounding tissue, according to some embodiments.

FIG. 3 illustrates a sagittal ultrasound image of a tendon injury after 4 weeks or repair, with labels for the tendon, scar tissue, adhesion, and the proximal and medial phalanges. The image structure is complex and traditional manual segmenting of scar tissue can be subjective and inconsistent.

Figure 4:
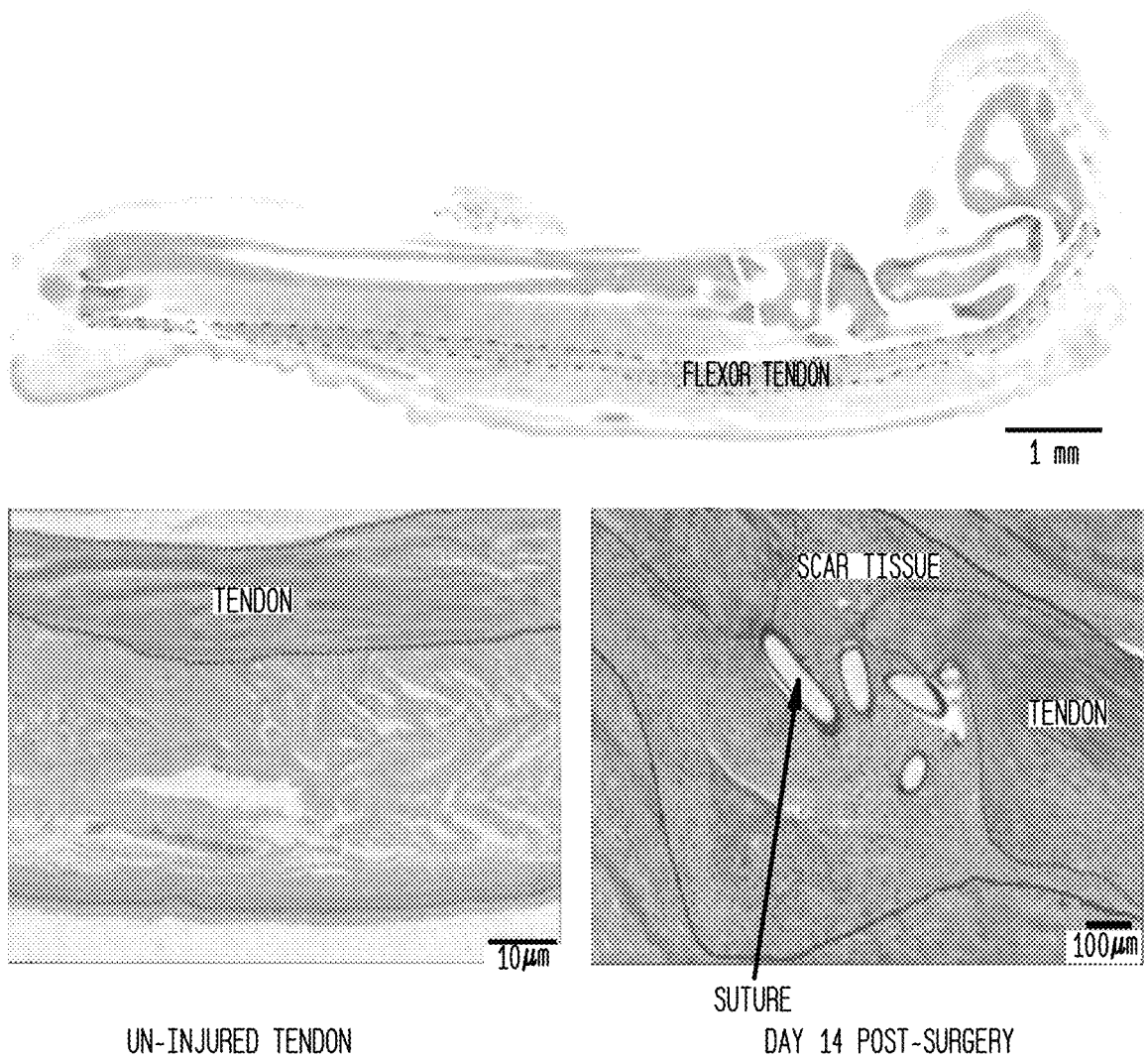
FIG. 4 illustrates histology views of a finger and tendon and scar tissue anatomy of a mouse paw before and after repair surgery.

FIG. 4 illustrates histology views of pertinent anatomy of a mouse paw. The top illustration shows and labels the flexor tendon, the lower left illustration shows and labels the un-injured tendon; and the lower-right illustration shows and labels anatomy 14 days post-surgery.

Figure 5:
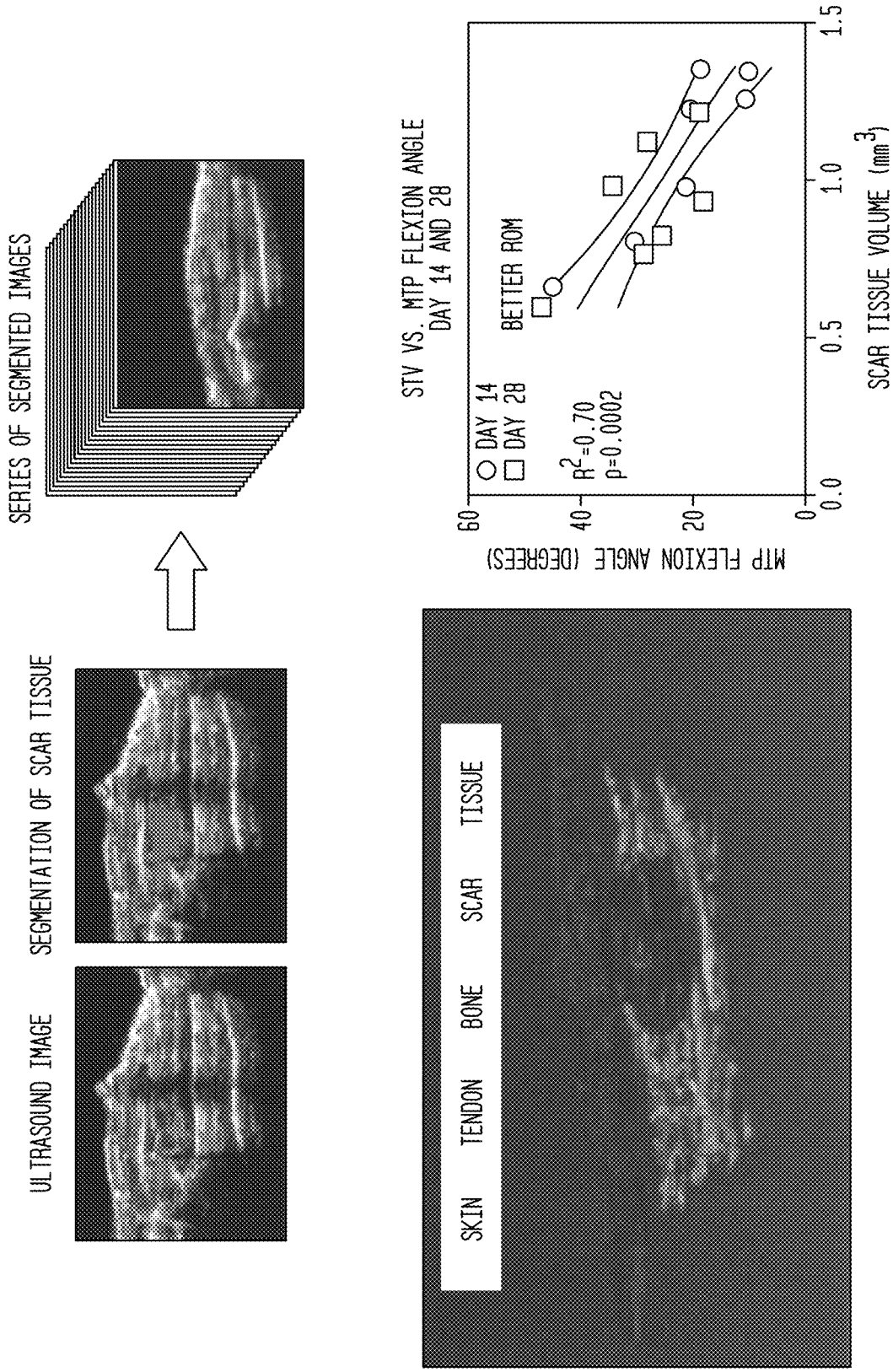
FIG. 5 illustrates several ultrasound images of a tendon of a mouse paw and a graph relating STV (scar tissue volume) to MTP (metatarsophalangeal) flexion angle, according to some embodiments.

FIG. 5 illustrates how metrics can objectively predict function following tendon injury. Upper left illustrates a sagittal ultrasound image, and the image to its right illustrates in red or shades of gray scar tissue that has been segmented from the image on the left. The segmentation can be done manually but preferably is done by applying computer-implemented segmentation algorithms to the image on the left, as discussed in more detail further below. Upper right illustrates a series of sagittal images forming a 3D view in which a volume of scar tissue is segmented. Lower left shows a sagittal view with skin, tendon, bone, and scar tissue shown in different colors or shades of gray and labeled. Lower right shows an example of graphs relating scar tissue volume (STV) vs. metatarsophalangeal (MTP) flexion angle for several clinical cases 14 days and 28 days after tendon injury and highlights an important relationship of non-invasively and objectively measured or estimated STV according to the processes described in this patent specification and flexion angle, which is a measure of healing.

Figure 6:
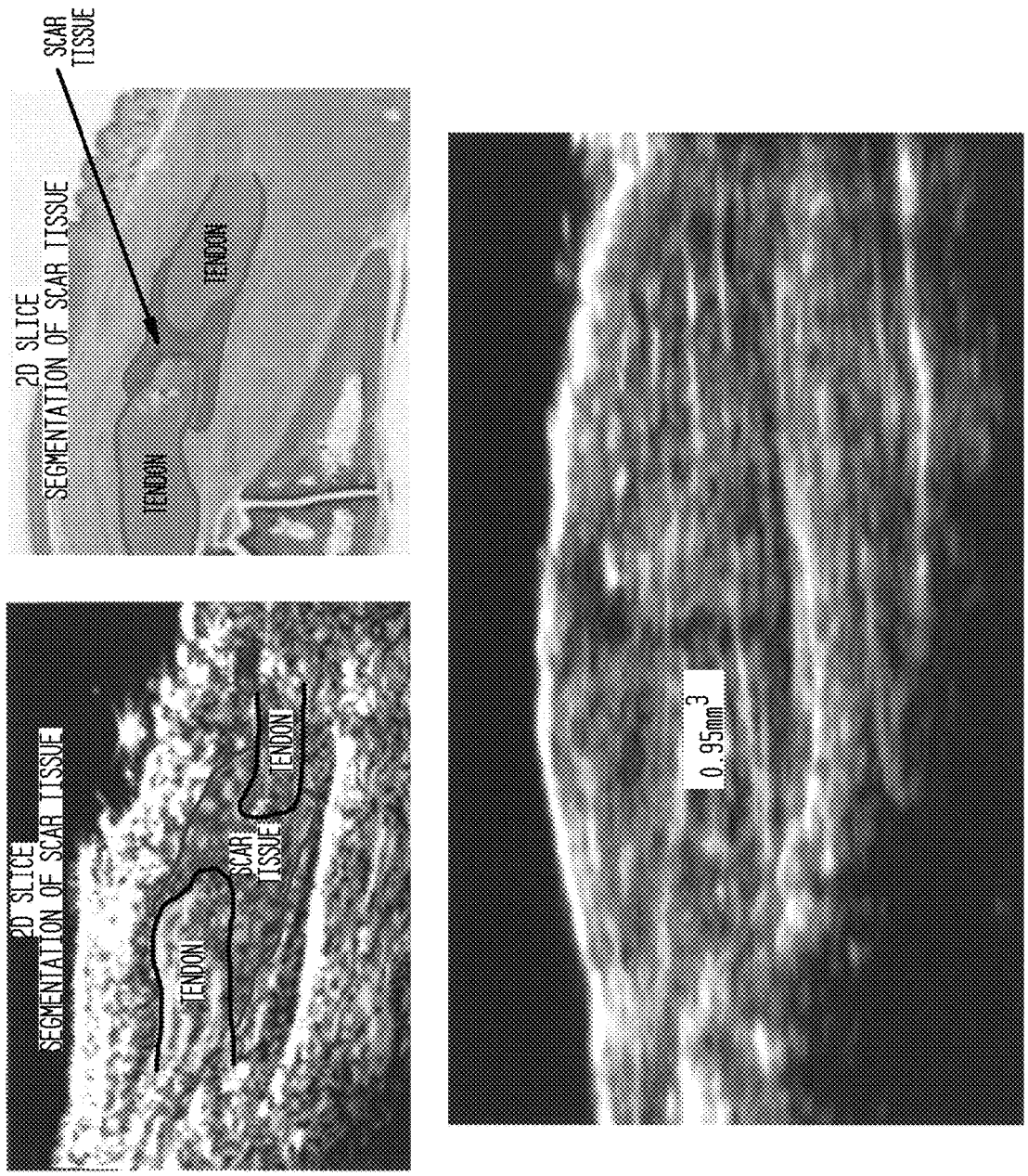
FIG. 6 illustrates an ultrasound image of a mouse paw tendon healing and an image with segmented types of tissue and a matching histology image, according to some embodiments.

FIG. 6 illustrates at upper left a result of segmenting an ultrasound sagittal view such as the lower image in FIG. 6. The upper left image shows in different colors or shades of gray and labels the scar tissue and the tendon. The segmentation preferably is done by applying computer-implemented segmentation algorithms to an image such as the lower image in FIG. 6. Upper right shows a histology image confirming that the segmentation seen at upper left is consistent with actual tissue.

Figure 7:
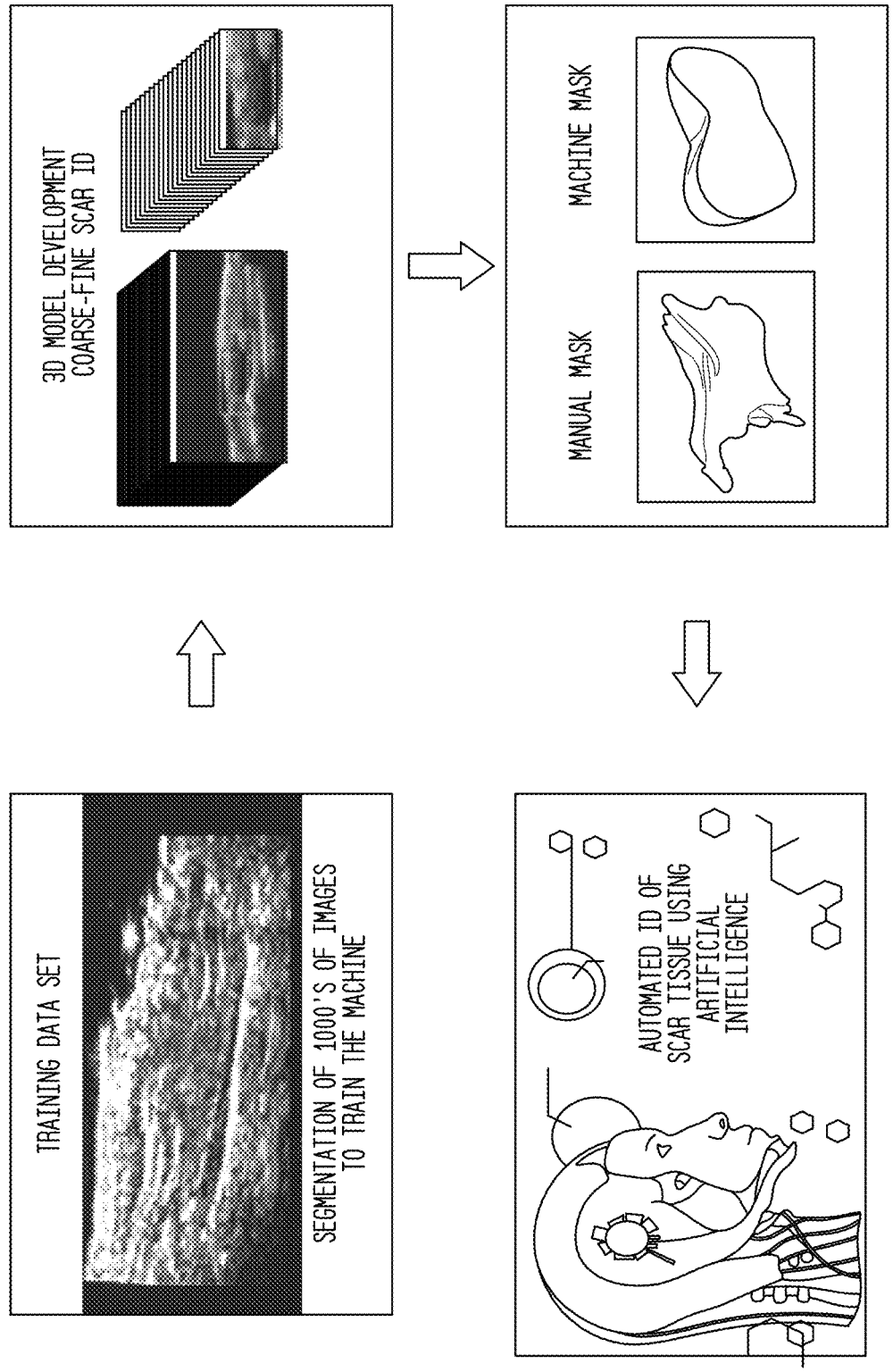
FIG. 7 illustrates stages of a process of using training sets of manually segmented ultrasound images for computer-implemented machine segmentation of new ultrasound images of tendon healing and computer-implemented artificial intelligence assessment of results, according to some embodiments.

FIG. 7 illustrates some of the steps in automated segmentation of scar tissue in ultrasound images acquired with equipment such as seen in FIG. 1 but for mouse paws. Upper left shows an example of a sagittal ultrasound image with scar tissue shown in green or a shade of gray that has been segmented manually, for use in a training set of images. This view is an example of thousands of similar views from different subjects at different stages of healing after tendon injury, in which scar tissue has been or would be segmented by experts using a consistent protocol. Upper right illustrates the development of a 3D model derived from images such as at upper left, where scar tissue is identified as a volume, again for use as a training set of 3D images of many subjects at different stages of healing. The training volumes can be at a single spatial resolution, or they can be one or more sets at coarser resolutions and one or more sets at finer resolutions (spatial and/or contrast). Lower right illustrates a "manual mask," i.e., a manually identified area of scar tissue in a training image of scar tissue in a sample subject, and a "machine mask," i.e., the outline of an area of scar tissue derived from the same image or images of a subject derived not manually but through application of computer-implements segmentation algorithms to ultrasound images of tendons and surrounding tissue. The masks are illustrated in 2D but can be shown in 3D or as 2D projections of 3D volumes or as synthesized sections through 3D volumes. Finally, lower left illustrates the automated, computer-implemented identification of scar tissue, preferably using artificial intelligence (AI) algorithms.

Figure 8:
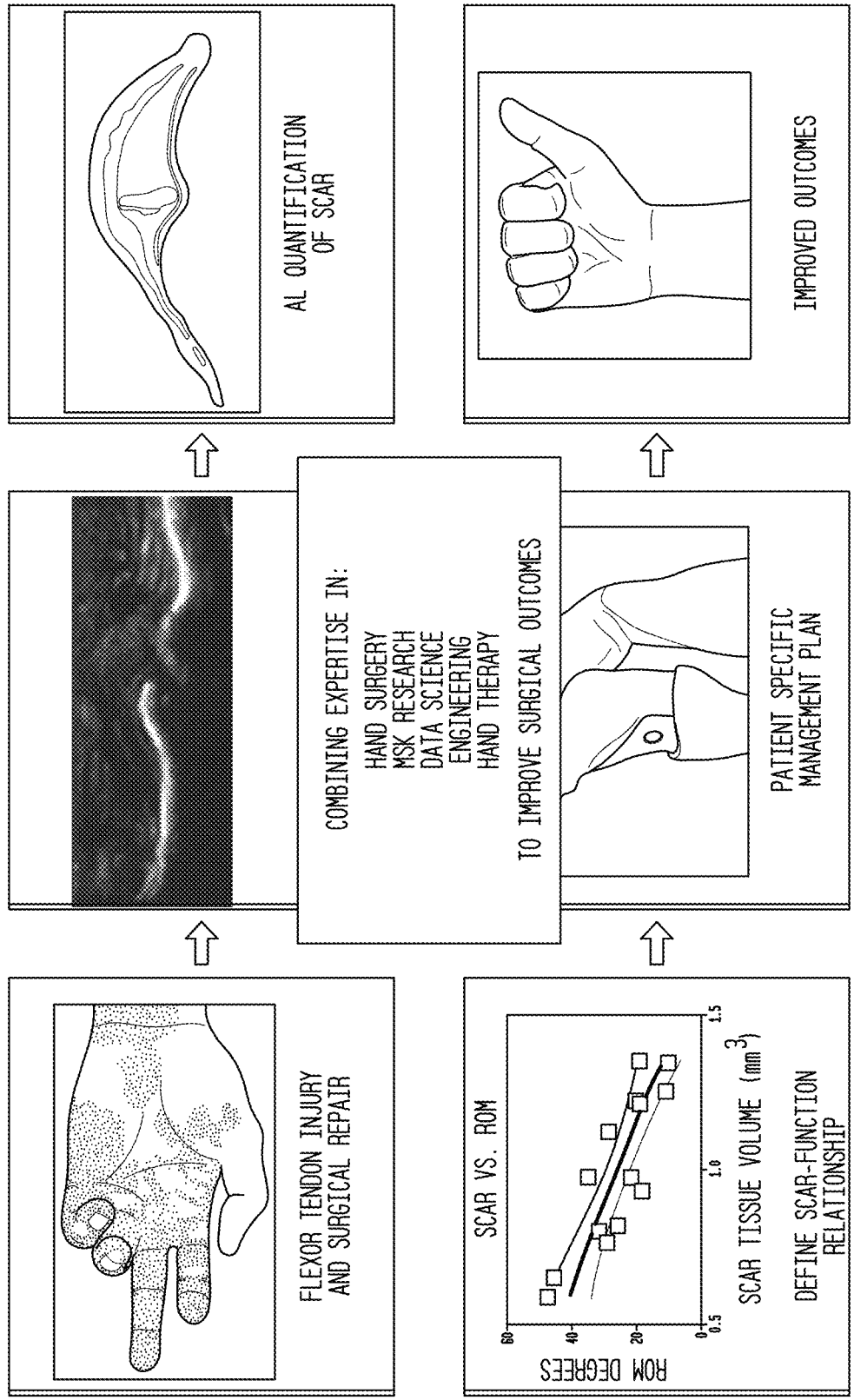
FIG. 8 illustrates stages of developing a computer-implemented predictive model of finger tendon healing.

FIG. 8 illustrates use of some of the results of the processes of FIG. 7. Upper left shows a finger with an injured tendon after a surgical repair. The middle upper image shows one of the ultrasound sagittal images of a finger after some period of healing such as 14 or 28 days. Upper right shows a quantification of the scar tissue in 2D or preferably in 3D derived by applying computer-implemented AI algorithms to images of fingers. Lower left shows a graph relating scar tissue volume (STV) to range of motion (ROM) for the fingers of patients, demonstrating that STV as measured or estimated as described in this patent specification is an objective and consistent predictor of ROM. The lower middle image points out that one of the benefits of the objective and consistent metric (STV) derived as described is to facilitate developing patient-specific management plans such as whether to do further surgery, whether to medicate and if so how, whether to start or continue physical therapy and if so what physical therapy protocol to use and over what time span and with what changes over time, what physical activity of the patient can be safely prescribed and how that can change over time, what disability level can be ascribed to the patient for employment or insurance purposes, etc. Lower right refers to improved outcomes for the patient due to better management of the injury using the equipment and methods described in this patent specification.

The computer-implemented segmentation of scar tissue can be implemented through computer algorithms using principles discussed for example in references (7-10). Preferably, such segmentation uses a training set comprising a multiplicity, for example thousands, of ultrasound images of fingers where each image includes a manually segmented area or volume of scar tissue and associated parameters related to known healing history and possibly other parameters such as finger size, age and sex of the person, duration of healing, etc. The computer-implemented segmenting facility tests a current 2D or 3D image of a patient's finger against this training set or against parameters derived from the training set to estimate a 2D or 3D size of scar tissue and provide the estimate, for example as a quantified STV value for the patient's finger. The training set can be further used to estimate how the STV for the patient compares with healing parameters such as ROM in the training set. For example, the training set can be formatted as a graph of STV vs. ROM or some other parameter of healing, with a band encompassing values for STV and ROM or another parameter that have been shown to fit good results for a patient from a selected medication type or dosage, or some other treatment such as a physical therapy course or additional surgery. A histogram of such STV vs. ROM values can be as illustrated in FIG. 8. Different such bands can be selected for different patient characteristics such as age. A display can be provided showing the STV vs. ROM point for a patient's finger and the appropriate band for a population of training images, as a guide for treatment or classification of an injury and healing process.

In one illustrative example of implementing a process according to principles described above, a high-frequency, high-resolution ultrasound platform imaged in vivo the healing flexor digitorum longus tendon in mice paws with a modified ultrasound scanner based on portions of equipment commercially available under the name Vevo® 3100, FUJIFILM VisualSonics Inc., Toronto, Canada. Ultrasound 3D images were uploaded into a platform commercially available under the name Amira (FEI v. 6.1.1, Hillsboro OR) and processed for segmentation and 3D reconstruction of native tendon and scar tissue to estimate scar tissue volume (Scar Tissue Volume; STV). The resulting STV estimates were correlated with current gold-standard metrics of tendon gliding function including Metatarsophalangeal (MTP) Range of motion (ROM) and Gliding Resistance (GR). The STV estimates strongly correlated positively with GR, and a strongly correlated inversely with MTP ROM.

The sensitivity of STV to differentiate between mouse model of healing with known differences in scar formation and restoration of gliding function was tested. It has been shown that S100a4GFP/+ mice heal with decreased scar formation and improved mechanical properties, relative to wildtype controls. Importantly, a significant reduction in STV was observed in S100a4 GFP/+ mice relative to wr, and STV was strongly correlated with MTP ROM, indicating that STV can serve as a non-invasive biomarker for tendon healing and can be usedas a rapid-screening tool to identify promising therapeutic targets in pre-clinical animal models.

Although the foregoing has been described in some detail for purposes of clarity, it should be clear that certain changes and modifications may be made without departing from the principles thereof. There can be alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims or permissible extensions thereof.

The following references are hereby incorporated by reference:
1. de Jong J P, Nguyen J T, Sonnema A J, Nguyen E C, Amadio P C, and Moran S L. The incidence of acute traumatic tendon injuries in the hand and wrist: a 10-year population-based study. *Clinics in orthopedic surgery.* 2014; 6(2): 196-202.
2. de Putter C E, Selles R W, Polinder S, Panneman M J, Hovius S E, and van Beeck E F. Economic impact of hand and wrist injuries: health-care costs and productivity costs in a population-based study. *J Bone Joint Surg Am.* 2012; 94(9):e56.
3. Galatz L M, Gerstenfeld L, Heber-Katz E, and Rodeo S A Tendon regeneration and scar formation: The concept of scarless healing. *J Orthop Res.* 2015; 33(6):823-31.
4. Beredjiklian P K. Biologic aspects of flexor tendon laceration and repair. *J Bone Joint Surg Am.* 2003; 85-A (3):539-50.
5. Lin T. Biomechanics of tendon inury and repair. *Journal of biomechanics.* 2004; 37:865-77.
6. Aydin A, Topalan M, Mezdegi A, Sezer I, Ozkan T, Erer M, et al. [Single-stage flexor tendoplasty in the treatment of flexor tendon injuries]. *Acta Orthop Traumatal Turc.* 2004; 38(1):54-9.
7. Shelhamer E, Long J, Darrell T. Fully Convolutional Networks for Semantic Segmentation. IEEE Trans Pattern Anal Mach Intell. 2017; 39(4):640-51.
8. Everingham M, Eslami S M A, Van Goal L, Williams C K I, Winn J, Zisserman A. The PASCAL Visual Object Classes Challenge: A Retrospective. Int J Comput Vision. 2015; 111(1):98-136.
9. Milletari F. V-Net: Fully Convolutional Neural Networks for Volumetric Medical Image Segmentation. arXiv. 2016; 1606.04797.
10. Betrouni N, Puech P, Dewalle A S, Lopes R, Dubois P, Vermandel M. 3D automatic segmentation and reconstruction of prostate on MR images. Conf Proc IEEE Eng Med Biol Soc. 2007; 2007:5259-62.
11. Wong J, Bennett W, Ferguson M W, McGrouther D A. Microscopic and histological examination of the mouse hindpaw digit and flexor tendon arrangement with 3D reconstruction. J Anat. 2006; 209(4):533-45.

The invention claimed is:

1. A system for ultrasound imaging of tendon regions comprising:
    an ultrasound image acquisition unit including an ultrasound transducer, a support for a patient's body part containing a tendon, a coupling agent for acoustic coupling of the transducer to the body part on the support, and an automated drive moving the transducer in a selected trajectory relative to the body part on the support to take ultrasound images thereof;
    an automated, computer-implemented segmentation facility configured to segment scar tissue from said images and/or from a three-dimensional representation of the imaged body part and derive a scar tissue estimate of the scar tissue in a selected volume of the body part;
    an automated, computer-implemented facility configured to test the scar tissue estimate against parameters derived from a multiplicity of teaching ultrasound images of the scar tissue associated with respective known tendon healing parameters and derive an estimate of expected healing parameters for the body part; and
    an automated, computer-implementing facility using the estimate of the expected healing parameter of the body part to provide one or more parameters pertaining to a treatment guide, medication dosing, and disability classification.

2. The system of claim 1, in which the body part is elongated and the ultrasound image acquisition unit is configured to scan the body part and provide a series of sagittal views spaced from each other along a width of the elongated body part by selected consistent intervals.

3. The system of claim 1, in which the body part is elongated and the ultrasound image acquisition unit is configured to scan the body part and provide a series of axial views spaced from each other along a length of the body part by selected consistent intervals.

4. The system of claim 1, in which the coupling agent comprises a liquid that is configured for the body part being imaged to be inserted in.

5. The system of claim 1, in which the body part is a patient's finger.

6. The system of claim 1, in which the ultrasound acquisition unit comprises a transducer holder and a motor driving the transducer holder along a selected trajectory to take said ultrasound images.

7. The system of claim 6, in which said transducer holder and motor are configured to take said ultrasound images at selected consistent spacing of the ultrasound images from each other.

8. The system of claim 6, in which said one or more parameters pertaining to the treatment guide, medication dosing, and disability classification comprise graphs relating scar tissue volume (STV) and metatarsophalangeal (MTP) flexion angle of a finger.

9. The system of claim 1, in which the automated, computer-implementing facility is configured to apply artificial intelligence algorithms to said estimates.

10. A method of ultrasound imaging of tendon regions comprising:
   acquiring ultrasound images of a body part that contains a tendon while supporting the body part and scanning the body part with an ultrasound transducer driven by a motor in a selected trajectory relative to the body part;
   segmenting scar tissue from said images and/or from a three-dimensional representation of a tendon in the imaged body part using an automated, computer-implemented image processing to derive a scar tissue estimate of the scar tissue in a selected volume of the body part;
   testing the scar tissue estimate and parameters derived from a multiplicity of teaching ultrasound images of the scar tissue associated with respective known tendon healing parameters and deriving an estimate of expected healing parameters for the tendon in said body part using an automated, computer-implemented facility; and
   using the estimate of the expected healing parameter of the tendon in said body part to provide one or more of a treatment guide, medication dosing, and disability classification with an automated, computer-implementing facility.

11. The method of claim 10, in which the body part is elongated and the acquisition comprises providing a series of sagittal views spaced from each other along a width of the body part by selected consistent intervals.

12. The method of claim 10, in which the body part is elongated and the acquisition unit is configured to provide a series of axial views spaced from each other along a length of the body part by selected consistent intervals.

13. The method of claim 10, in which the body part is a patient's finger.

14. The method of claim 10, in which said testing comprises comparing the scar tissue estimate with estimates based on known relationships between scar tissue and tendons to produce a treatment plan for the body part.

15. An apparatus comprising:
   a support for a body part comprising a hand and/or one or more fingers; an ultrasound transducer; a coupling medium configured to acoustically couple the ultrasound transduced to a selected portion of the body part and transmit ultrasound energy from the ultrasound transducer into the body part and from the body part into the ultrasound transducer; a transducer holder configured to hold the ultrasound transducer; a motor coupled with the transducer holder and configured to move the transducer holder and thus the ultrasound transducer relative to the body part along a selected trajectory;
   a control coupled with the transducer holder and the ultrasound transducer and configured to cause the ultrasound transducer to produce selected ultrasound images of the body part;
   a computer-implemented ultrasound engine coupled with the transducer and configured to process said ultrasound images into processed images;
   a computer-implemented segmentation engine configured to apply segmentation algorithms to said processed images to thereby identify tendons and scar tissue in said body part represented in said processed images;
   a computer-implemented quantification engine coupled with said segmentation engine and configured to quantify the tendons and scar tissue identified by the segmentation engine and produce quantification results;
   a storage storing a training image set and known relationships between tendon and scar tissue parameters and parameters related to healing;
   a computer-implemented results generator coupled with said quantification engine and said training image set and known relationship and configured to cause an interaction between said quantification results and said known relationship and produce results indicative of properties of said body part.

16. The apparatus of claim 15, in which the control is configured to cause the transducer holder to move along a length of a finger and to cause the ultrasound transducer to produce axial images of the finger spaced by selected distances along the length of the finger.

17. The apparatus of claim 15, in which the control is configured to cause the transducer holder to move across a length of a finger and to cause the ultrasound transducer to produce sectional images of the finger spaced by selected distances along a width of the finger.

18. The apparatus of claim 15, in which the said coupling medium is configured to immerse the body part and at least a portion of the ultrasound transducer therein.

19. The apparatus of claim 15, in which said processed images are three-dimensional images of tendons and scar tissue.

20. The apparatus of claim 15, in which said results comprises graphs relating scar tissue volume (STV) and metatarsophalangeal (MTP) flexion angle of a finger.

* * * * *